(12) United States Patent
Kuramoto et al.

(10) Patent No.: US 6,805,484 B2
(45) Date of Patent: Oct. 19, 2004

(54) HANDLE FOR DIGITAL RADIOGRAPHY PANEL

(75) Inventors: Yasushi Kuramoto, Aliso Viejo, CA (US); Tsuneo Imai, Irvine, CA (US); Junichi Yamayoshi, Newport Beach, CA (US); Keith O. Gillams, Anaheim, CA (US); Kristine D. Gerhards, Orlando, FL (US)

(73) Assignee: Canon U.S.A., Inc., Lake Success, NY (US)

( * ) Notice: Subject to any disclaimer, the term of this patent is extended or adjusted under 35 U.S.C. 154(b) by 104 days.

(21) Appl. No.: 10/326,510

(22) Filed: Dec. 19, 2002

(65) Prior Publication Data

US 2004/0120460 A1 Jun. 24, 2004

(51) Int. Cl.[7] .............................................. H01J 31/50
(52) U.S. Cl. ...................................... 378/189; 378/182
(58) Field of Search .............................. 378/98.8, 102, 378/182–190; 250/370.09, 580, 581

(56) References Cited

U.S. PATENT DOCUMENTS

| 5,661,309 | A | | 8/1997 | Jeromin et al. |
|---|---|---|---|---|
| 5,877,501 | A | | 3/1999 | Ivan et al. |
| 6,155,713 | A | * | 12/2000 | Watanabe ..................... 378/197 |
| 6,296,386 | B1 | * | 10/2001 | Heidsieck et al. ........... 378/189 |
| 6,447,164 | B1 | * | 9/2002 | Polkus ........................ 378/206 |
| 6,630,676 | B2 | * | 10/2003 | Takemoto .............. 250/370.09 |
| 2003/0202635 | A1 | * | 10/2003 | Boomgaarden et al. ..... 378/177 |

* cited by examiner

Primary Examiner—Craig E. Church
Assistant Examiner—Jurie Yun
(74) Attorney, Agent, or Firm—Canon U.S.A. Inc. Intellectual Property Dept.

(57) ABSTRACT

A portable device for recording X-ray images. The device comprising an X-ray image capture panel, a housing member connected to and surrounding the X-ray capture panel, at least a first handle secured to the housing member, means moveably connected to the at least first handle for moving the handle from a position parallel to the plane of the portable device to a position perpendicular to the plane of the portable device and from a position perpendicular to the plane of the portable device to a position parallel to the plane of the portable device. An accessory for carrying or holding the portable device, wherein the accessory is in the form of a frame secured to the portable device or a cover that portable device is placed within.

32 Claims, 16 Drawing Sheets

HANDLE FOR DIGITAL RADIOGRAPHY PANEL

BACKGROUND OF THE INVENTION

1. Field of the Invention

The invention relates to a filmless, self-contained, portable device for capturing X-ray images. More particularly, the invention relates to a handle for holding and positioning the portable device.

2. Description of the Related Art

Digital radiography (DR) systems have grown in popularity over the past number of years. Some DR systems include a portable flat panel image detector connected to a power supply or other power source as well as well as to an image processor or control computer. DR systems facilitate the production of direct, digital x-ray image information by transferring the x-ray image information captured by the flat panel to the image processor or control computer. In most instances, the image processor or control computer is connected to a picture archiving and communications system (PACS) network.

Because of its portable design, the flat panel image detector can be freely positioned in relation to the patient's anatomy, just like traditional screen-film cassettes. This portability makes it especially useful for trauma imaging as well as neonatal, pediatric, and orthopedic applications. Patients who have limited mobility can also be readily x-rayed. The compact feature of the portable flat panel allows for easy capture of images at angles that are difficult to set with fixed devices. Lateral and axial imaging of limbs, shoulders, the skull, the neck, and extremities are supported. Quick positioning is another benefit, as the portable flat panel is light enough for a radiologic technologist or patient to hold in place. Current flat panels include a single fixed handle for carrying and positioning the panel. The handle is either integrated into the structure of the panel itself, or affixed to one side of the panel.

Existing portable flat panel image detectors are approximately 13"×13", with image capture area of 9"×11", and weigh approximately 6.2 lbs (2.8 kg). The image capture area includes among other things a sensor panel and an analog/digital conversion board. The image capture area also includes lead, which makes up most of the panels weight. Lead is necessary to reduce the intensity of the X-ray as it passes through the sensor panel. For example, as shown in FIG. 10, when the X-ray 35 enters the image capture area of the flat panel image detector 36, the sensor plate 37 absorbs a certain amount of the X-ray, forming an image. The lead 38 prevents the X-ray not absorbed by sensor plate from hitting anything or anyone located behind the flat panel image detector. Because of the small image capture area, there is not a need for a large amount of lead 38. Thus, one handle is sufficient to hold and position flat panel image detectors with this dimension and weight.

There is a need for portable flat panel image detectors that are larger than the current image detectors. As the flat panel image detectors become larger, the amount of lead they contain increases accordingly. The additional lead makes these panels heavier and more difficult to manage. A single handle is not sufficient to use to hold and position these larger flat panel image detectors. What is needed is a mechanism for making it easier to hold and position larger flat panel image detectors.

SUMMARY OF THE INVENTION

It is an object of the foregoing invention to address the foregoing difficulty by providing a handle structure for holding and positioning large DR portable flat panel image detectors.

In one aspect, at least one handle is secured in hinged relation to a portable DR flat panel image detector. The handle is hingedly moveable from a position parallel to the plane of the panel, hereinafter referred to as zero-degree position to a position perpendicular to the plane of the panel, hereinafter referred to as 90-degree position. Hinged movement of the handle is preferably obtained by a user (i.e., radiologic technologist) moving the handle from the zero-degree position to the 90-degree position and from the 90-degree position back to the zero-degree position. By virtue of the hinged movement of the handle, a user can easily move and place a DR flat panel image detector in relation to a patient's anatomy to take an X-ray.

In yet another aspect, at least two handles are secured in hinged relation to a portable DR flat panel image detector. At least a first handle is secured to a horizontal side of the DR flat panel image detector and the at least second handle is secured to a vertical side of the DR flat panel image detector. Providing at least two handles provides the user with even better control when positioning the DR flat panel image detector in relation to a patient's anatomy to take an X-ray.

This brief summary has been provided so that the nature of the invention may be understood quickly. A more complete understanding of the invention can be obtained by reference to the following detailed description of the preferred embodiment(s) thereof in connection with the attached drawings.

DETAILED DESCRIPTION OF THE PREFERRED EMBODIMENTS

Figure 1:
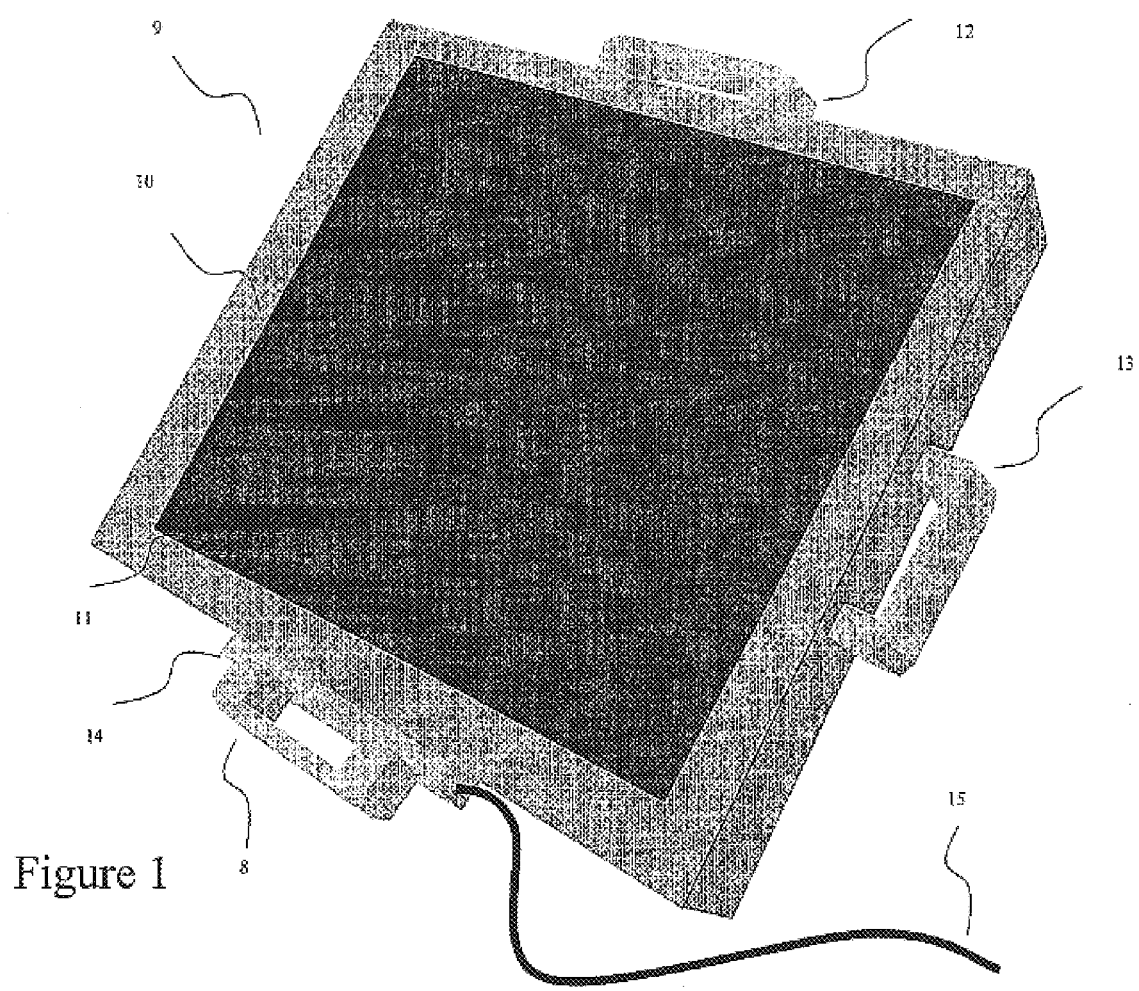
FIG. 1 is a front perspective of the preferred embodiment of the portable device of the present invention.
Figure 6:
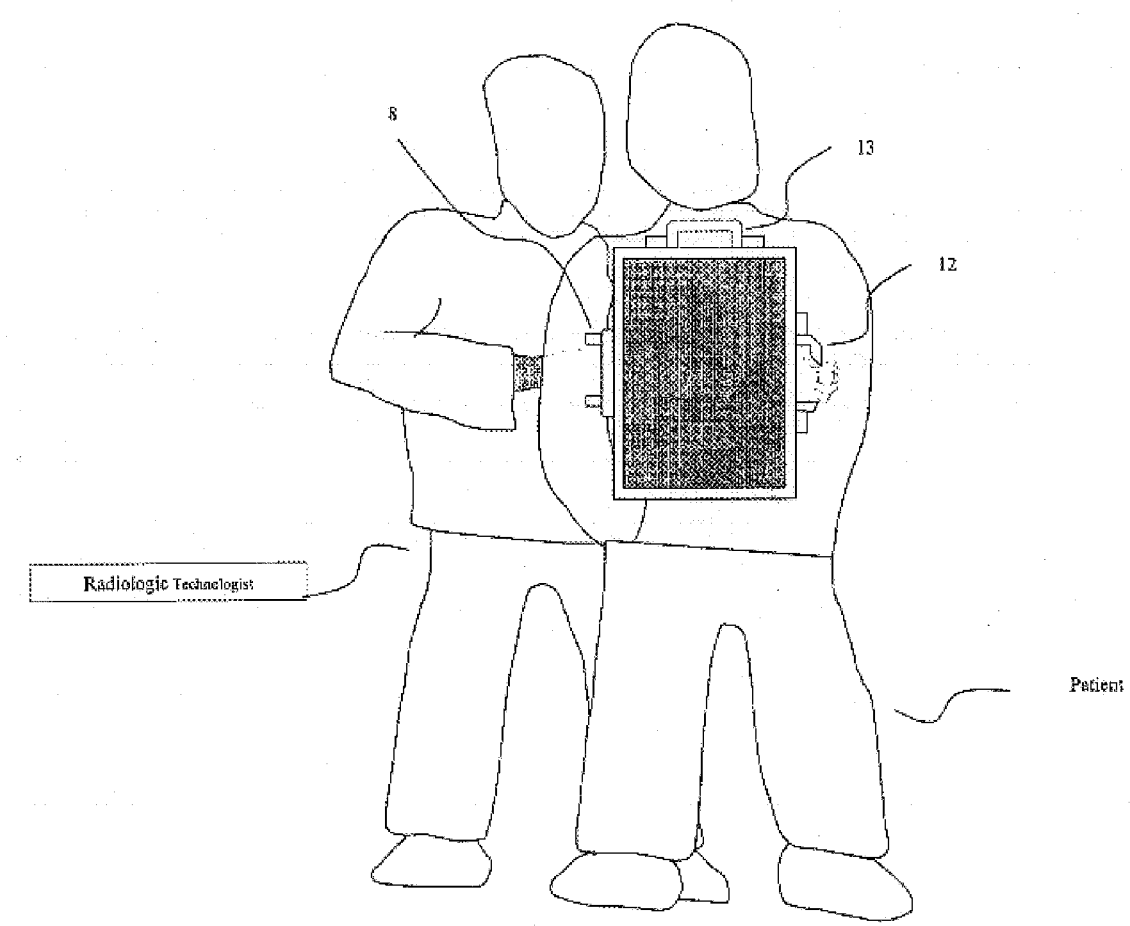
FIG. 6 depicts use of the portable device of the present invention in a first orientation.
Figure 7:
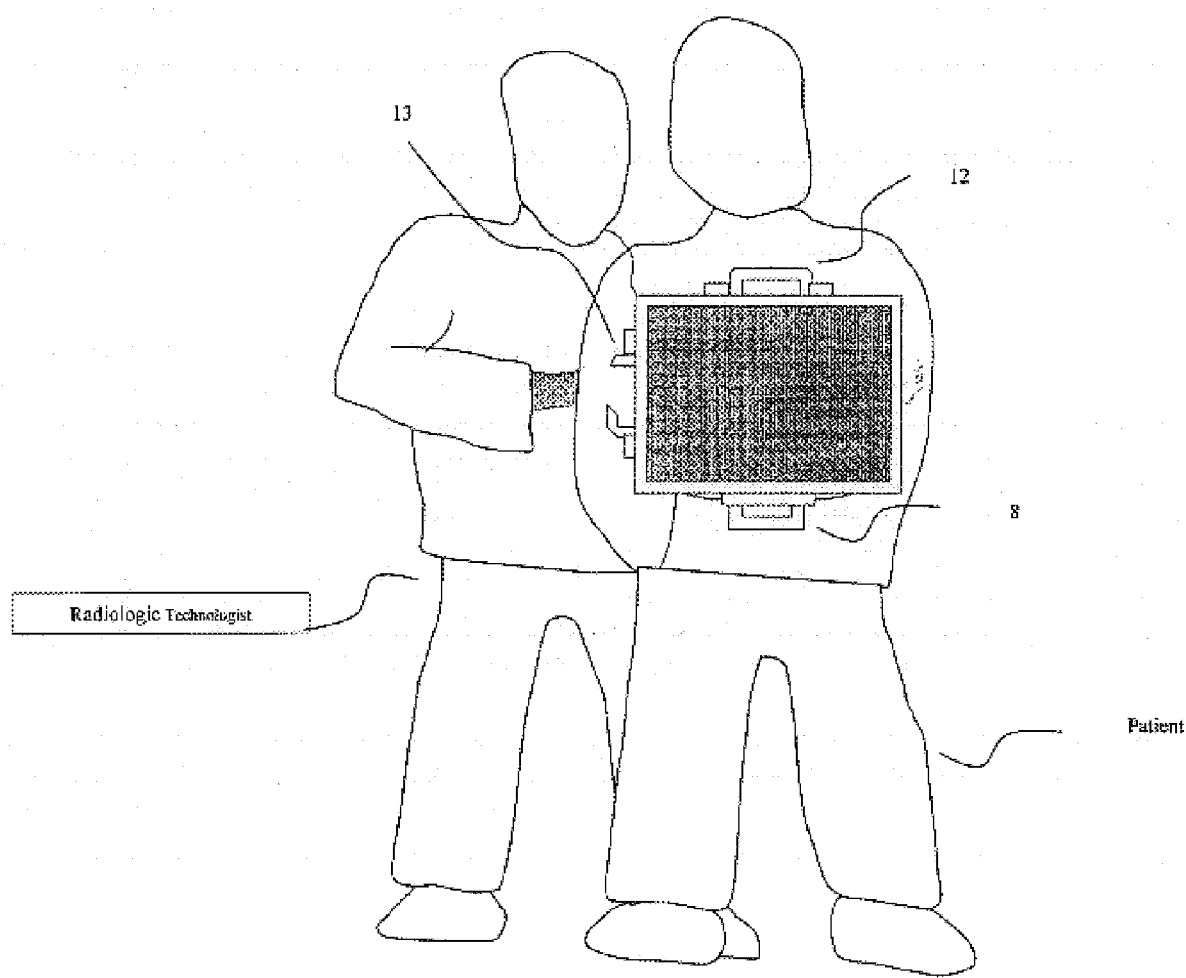
FIG. 7 depicts use of the portable device of the present invention in a second orientation.

FIG. 1 is a front perspective of the preferred embodiment of the portable device of the present invention. Portable device 9 consists of an outer housing 10 connected to and surrounding an inner plate 11. Outer housing 10 is composed of plastic, aluminum, lead, and carbon. However, the composition of outer housing 10 is not limited to these materials. Inner plate 11 is a high-resolution flat panel detector composed of a high-precision amorphous silicon (a-Si) and a thin film transistor (TTF) array. Interface cable port 14 is secured to one side of outer housing 10 and connected to interface cable 15. Interface cable 15 connects portable device 9 to a control station (not shown), which is typically an image processor. The control station allows a radiologic technologist to view images captured by portable device 9 and transmitted via interface cable 15, and can be connected to a picture archiving and communication system (PACS) network. Handles 12, 13 are secured to separate sides of outer housing 10, different from the side that interface cable port 14 is secured to. In the preferred embodiment, handle 12 is located on the side opposite the side interface cable port 14 is secured to, and handle 13 is located on one of the two remaining sides. In addition, handles 12, 13 are preferably located in the center of their respective sides. Centering handles 12, 13 provides for even balancing of portable device 9 when in use, as well as ease of use by the user. For example, as shown in FIG. 6, centering of handle 12 allows a radiologic technologist to easily position portable device 9 with respect to a patient. FIG. 7 is another example of how the centered position of handles 12, 13 allows a user to easily position portable device 9 with respect to a patient. The preferred material of handles 12, 13 is plastic, but is not limited to plastic and any material that would allow practice of the present invention would be applicable. Handle 8 is connected to interface cable port 14. The method of securing handles 12,13 to outer housing 10 is discussed below with respect to FIGS. 4 and 5.

Figure 2:
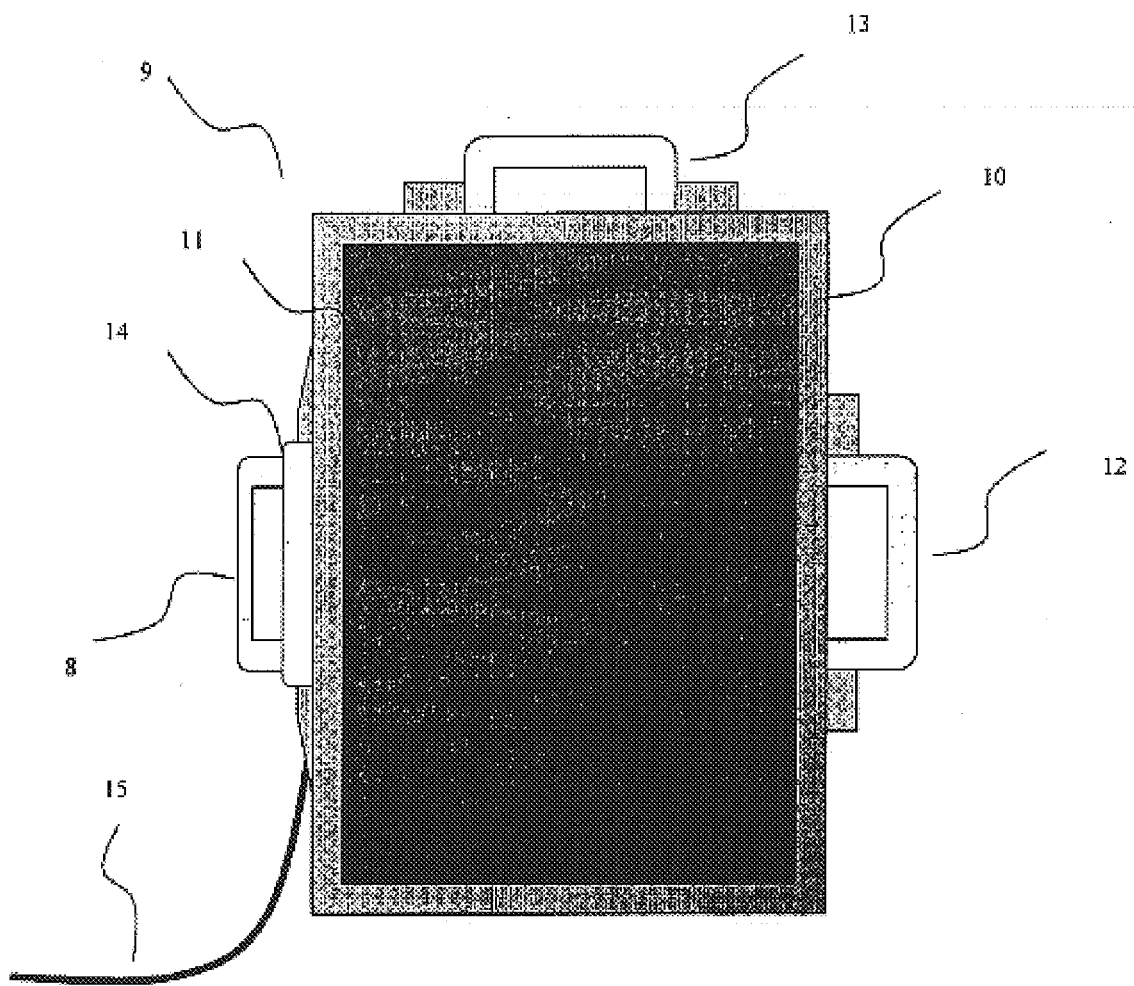
FIG. 2 is a top-down perspective of the preferred embodiment of the portable device of the present invention.
Figure 3:
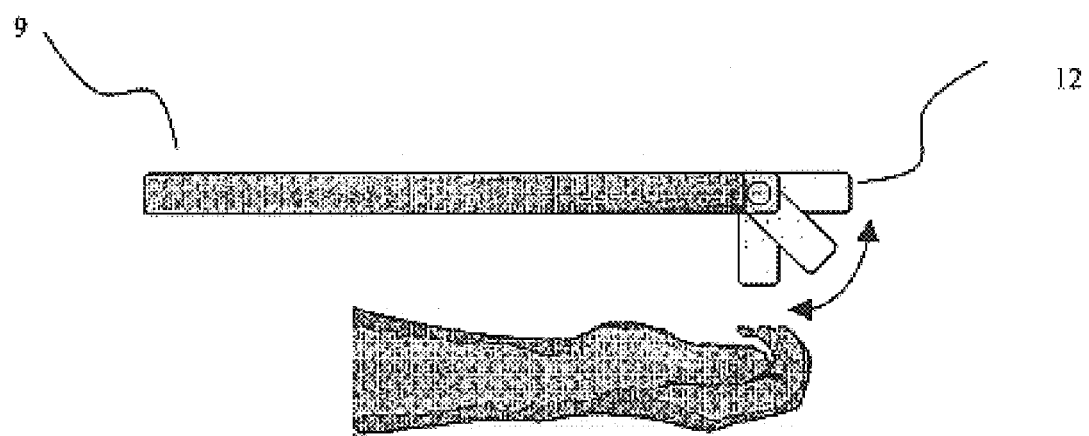
FIG. 3 is a side perspective of the preferred embodiment of the portable device of the present invention.
Figure 4:
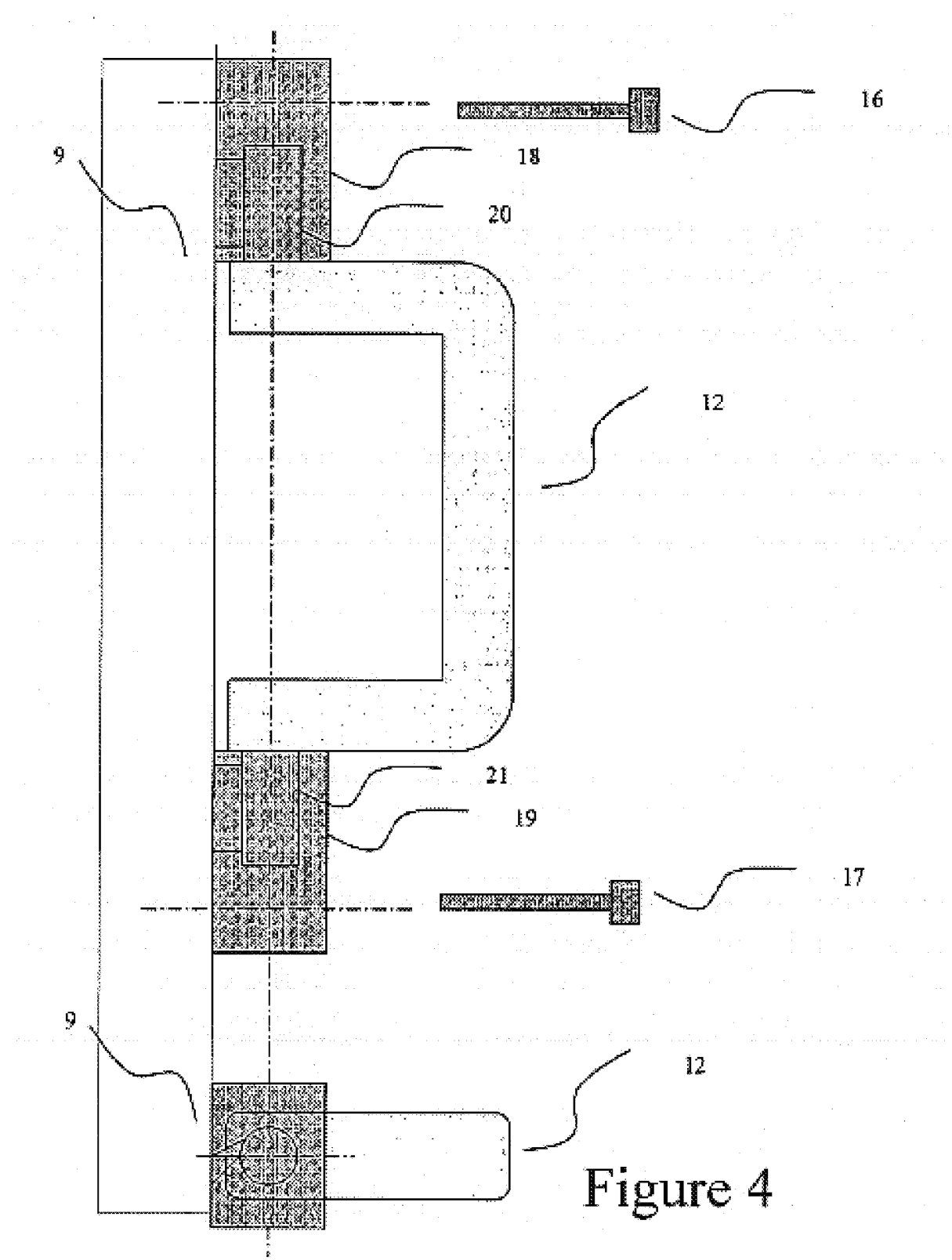
FIG. 4 is a cross-sectional view of the preferred embodiment of the means for moveably connecting handle(s) to the portable device of the present invention.

FIG. 2 is a top-down perspective of the preferred embodiment of portable device 9. FIG. 3 is a side perspective of portable device 9. More specifically, FIG. 4 depicts movement of handle 12 with respect to portable device 9. A more detailed description of this movement is provided below with respect to FIGS. 4 and 5.

FIG. 4 is a cross-sectional view of the preferred embodiment of the means for moveably connecting handles 12, 13 to portable device 9 of the present invention. Briefly, handles 12,13 are moveably connected to portable device 9 in order for a user to more easily hold and/or position portable device 9 with respect to a patient's anatomy when taking an X-ray of the patient. The following description of the means for moveably connecting handles 12, 13 to portable device 9 references handle 12. The same means apply to handle 13.

In more detail, handle 12 includes two shafts 20, 21 connected perpendicularly to each of the legs of handle 12. Shafts 20, 21 are enclosed by stoppers 18, 19 respectively, and affixed to outer housing 10 of portable device 9. Stoppers 18, 19 are secured to outer housing 10 of portable device 9 by screws 16, 17 respectively.

Figure 5:
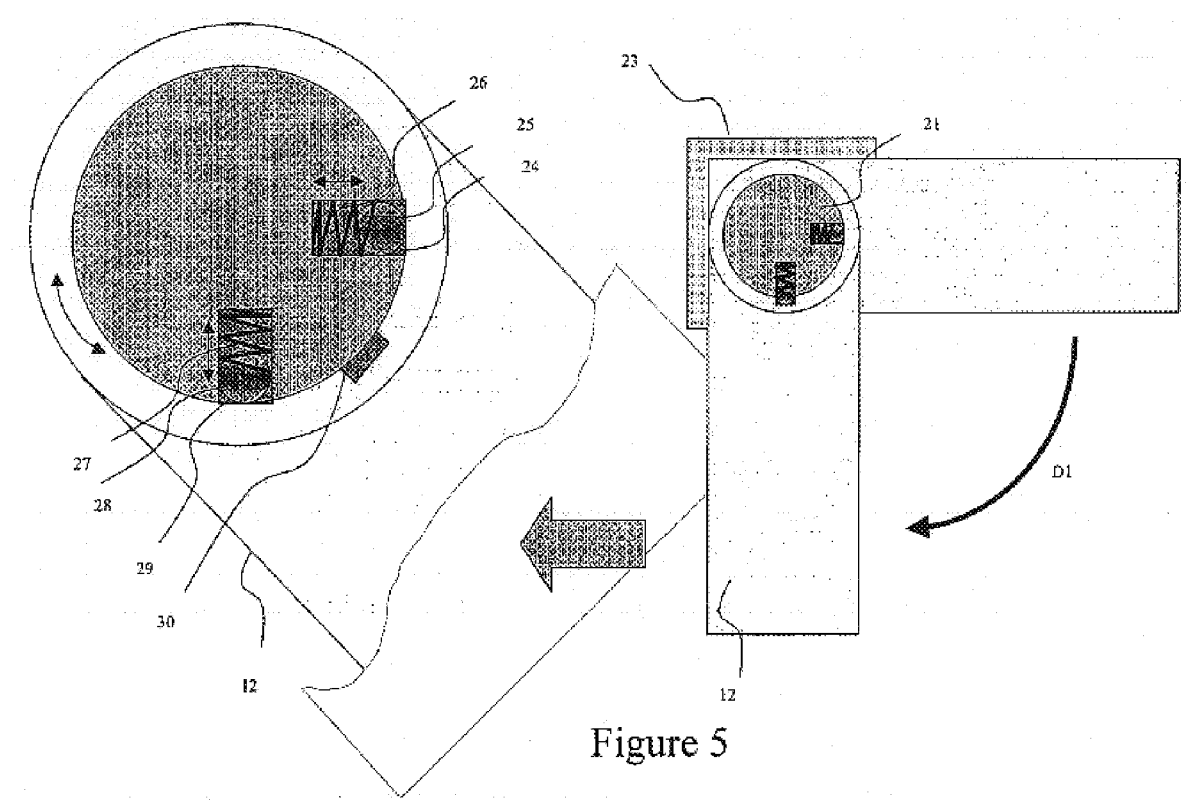
FIG. 5 is a cutaway view of the preferred embodiment of the means for moveably connecting handle(s) to the portable device of the present invention.

FIG. 5 is a cutaway view of the preferred embodiment of the means for moveably connecting handle(s) 12, 13 to portable device 9 of the present invention.

In more detail, shaft 21 contains two openings 24, 29 that are located 90 degrees from one another. Contained in each opening are springs 26,27 and ball bearings 25, 28 respectively. Both springs 26, 27 and ball bearing 25, 28 have the same diameter has openings 24, 29. Handle 12 includes opening 30, which has the same diameter as openings 24, 29 and its depth is equivalent to radius of ball bearings 25, 28.

When handle 12 is in the zero-degree position (parallel to the plane of portable device 9), opening 30 is aligned with opening 24. When opening 30 is aligned with opening 24, ball bearing 25 is moved out of opening 24 by spring 26 and into opening 30. Since the depth of opening 30 is equivalent to the radius of ball bearing 25, one half of ball bearing 25 is positioned in opening 30 and the other half remains positioned in opening 24. The location of ball bearing 25 locks handle 12 in the zero-degree position.

When pressure is applied to handle 12 and handle 12 is rotated in direction D1, ball bearing 25 moves away from opening 24 and completely back into opening 30. When handle 12 reaches 90-degree position (perpendicular to the plane of portable device 9), opening 30 aligns with opening 29. Alignment of opening 29 and 30 results in spring 27 moving ball bearing 28 out of opening 29 and into opening 30. Since the depth of opening 30 is equivalent to the radius of ball bearing 28, one half of ball bearing 28 is positioned in opening 30 and the other half remains positioned in opening 29. The location of ball bearing 28 locks handle 12 in the 90-degree position.

Handle 12 can be returned from the 90-degree position to the zero-degree position by applying pressure to handle 12 and rotating in the direction opposite direction D1. Stopper 21 works in conjunction with ball bearings 25, 29 to prevent handle 12 from moving past the zero-degree or 90-degree positions.

Figure 8:
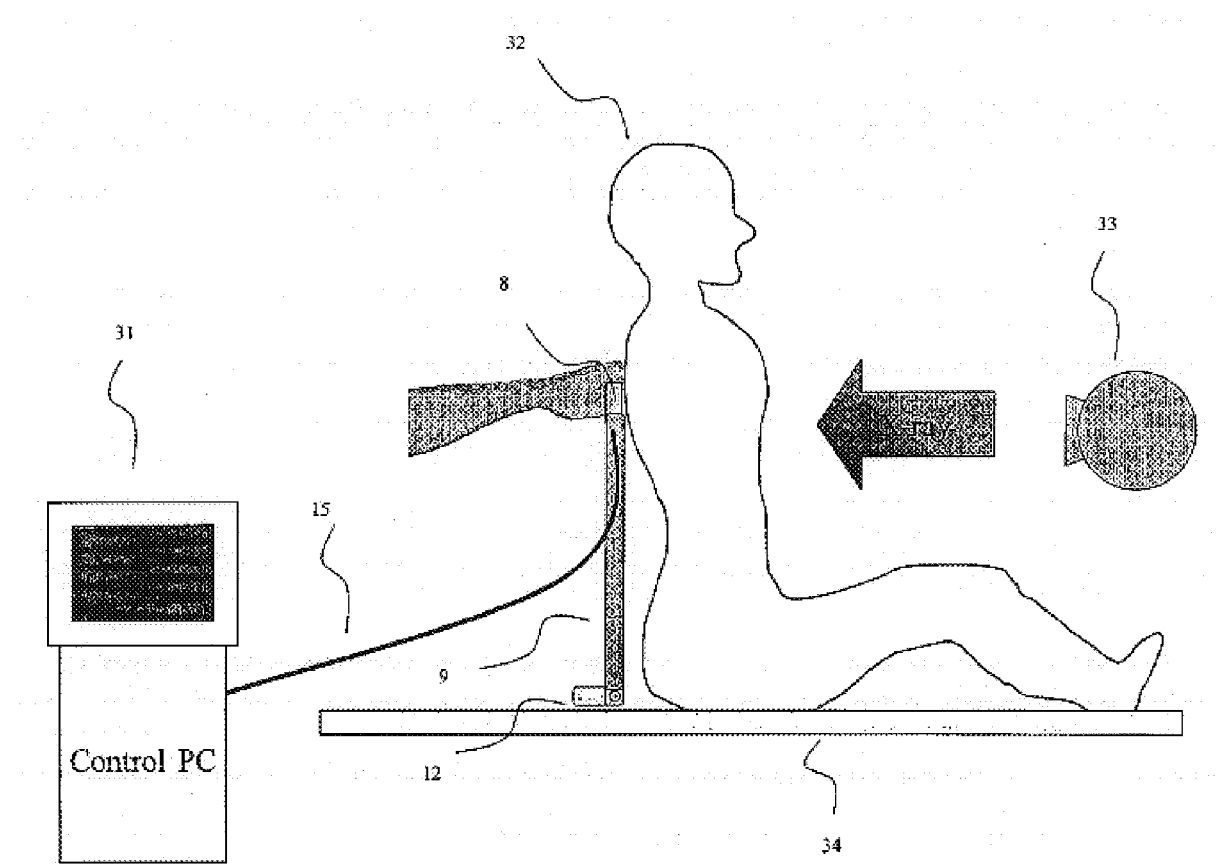
FIG. 8 depicts use of the portable device of the present invention in a third orientation.

FIG. 8 illustrates using portable device 9 where handle 12 is in the 90-degree position. Portable device 9 is placed behind a patient 32 sitting upright on X-ray table 34 and directly across from X-ray machine 33. In order to easily position portable device 9 given patient's 32 positions with respect to X-ray machine 33 and X-ray table 34, handle 12 is placed in the 90-degree position. The image captured by portable device 9 is transmitted via interface cable 15 to control computer 31. As described above, control computer 31 allows for among other things, a radiologic technologist to view the captured image transmitted via interface cable 15. In addition, control computer 31 can be connected to a picture archiving and communication system (PACS).

Figure 9:
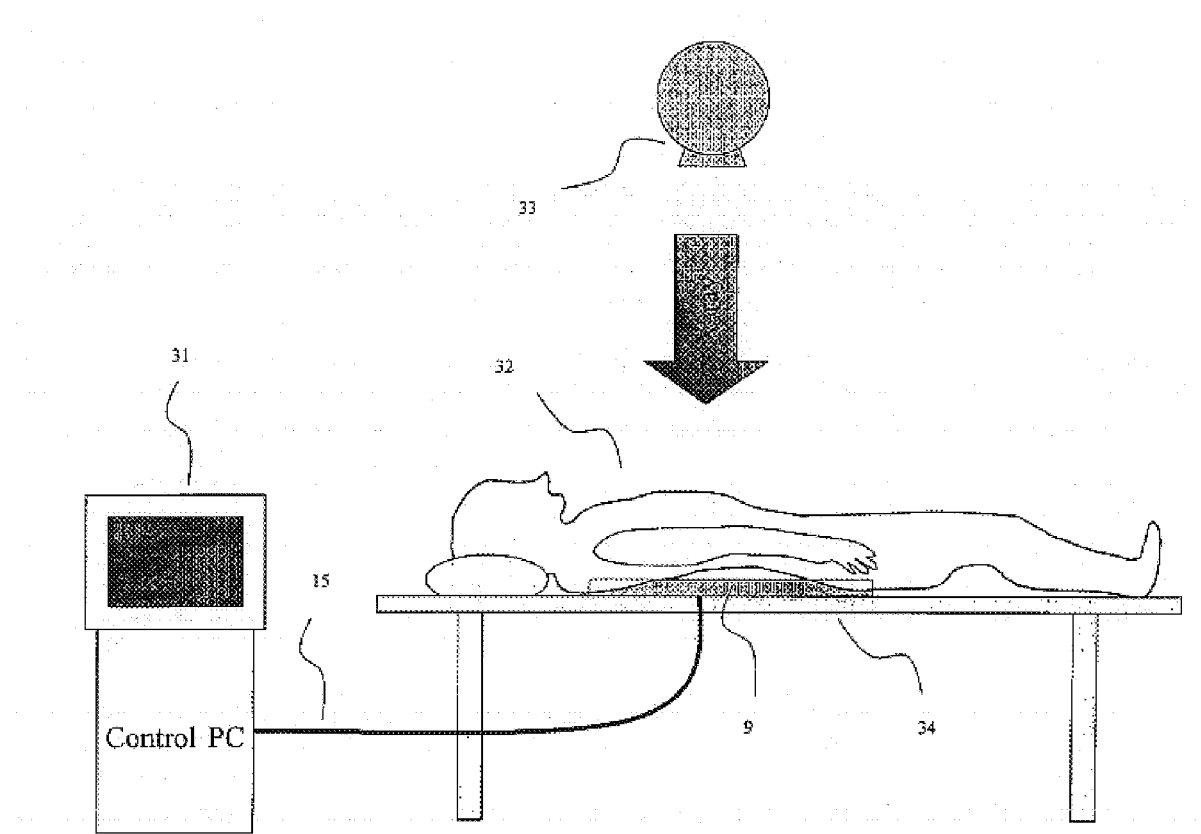
FIG. 9 depicts use of the portable device of the present invention in a fourth orientation.
Figure 10:
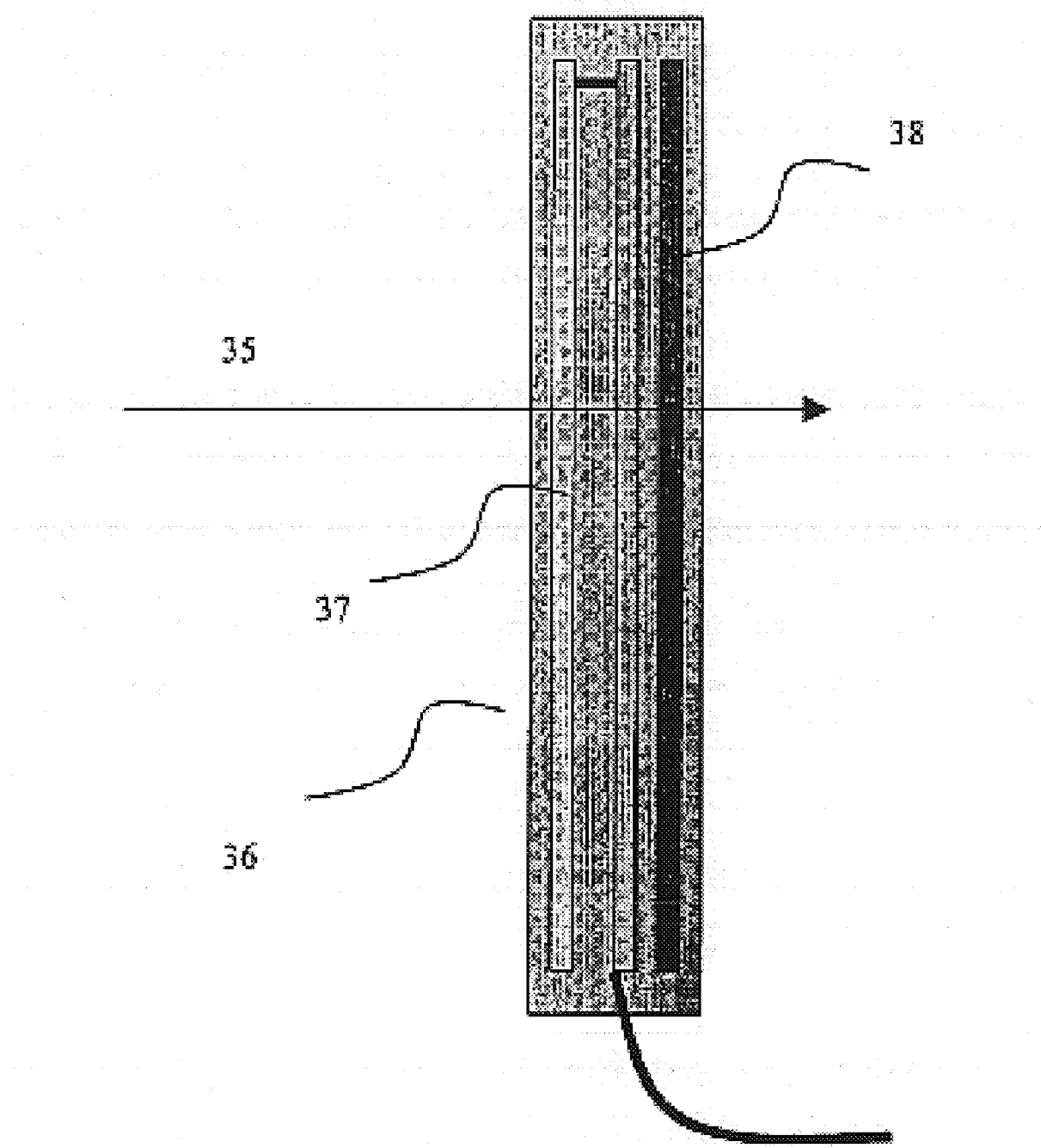
FIG. 10 is a cross-sectional view of a flat panel image detector.

FIG. 9 provides another use of portable device 9 where handles 12, 13 (not shown) are in zero-degree position. In this configuration, portable device 9 is placed flat under patient 32 while patient is lying on X-ray table 34. As previously described, interface cable 15 is used to transmit the image captured by portable device 9 to control computer 31.

The above embodiment of the present invention includes handle 8 connected to interface cable port 14. In another embodiment, handle 8 is not present. In another embodiment, in addition to handles 12, 13, an additional handle is moveably connected to the side of outer housing 10 opposite the side handle 13 is connected to. In still yet another embodiment, only a single handle is moveably connected to outer housing 10.

Figure 11:
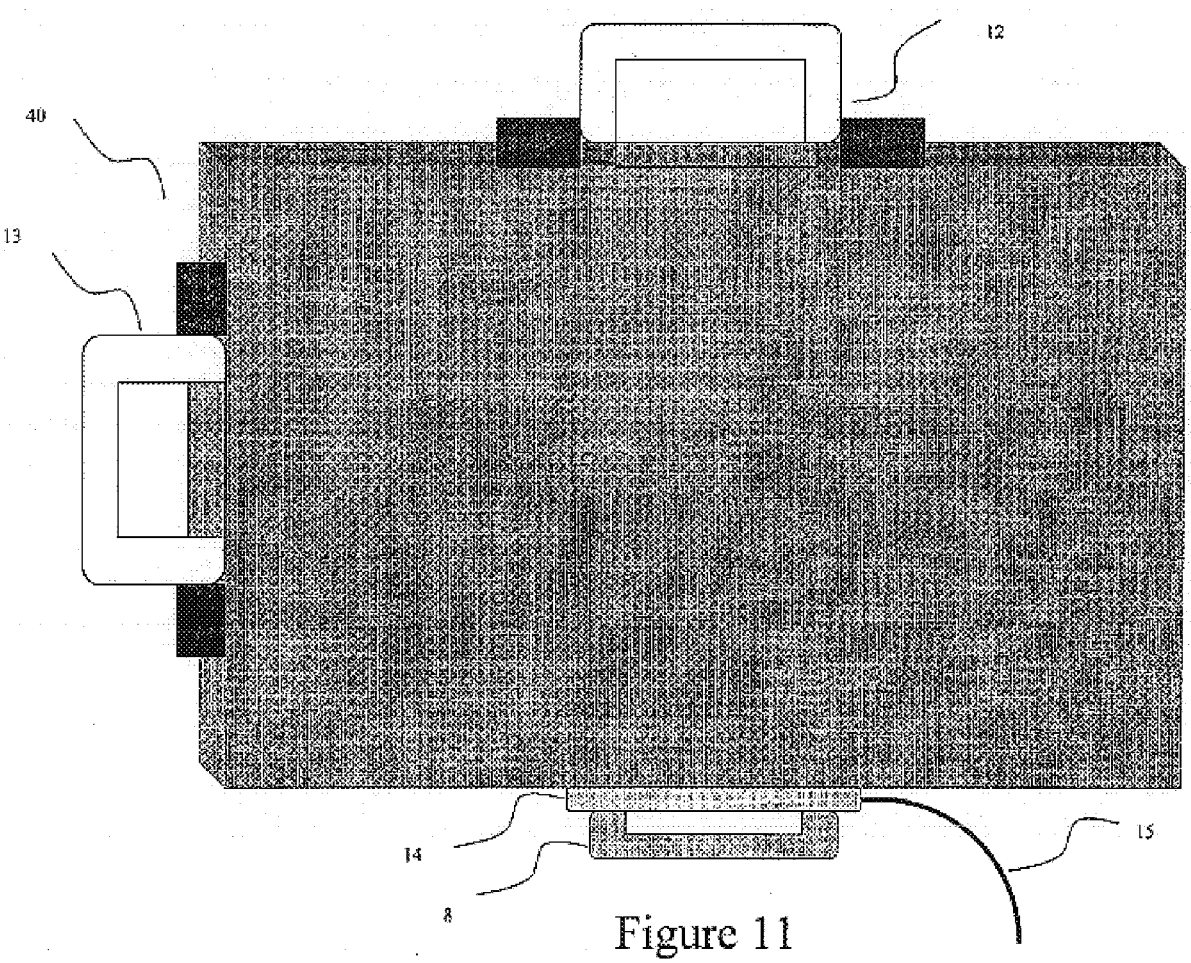
FIG. 11 depicts the front view of a first accessory to the portable device of the present invention in use with the portable device.

FIG. 11 depicts the front view of a first accessory to the portable device of the present invention in use with the portable device. More specifically, FIG. 11 depicts a protective cover 40 that fits over portable device 9 to protect inner plate 11. Protective cover 40 contains three openings (not shown) that allow access to handles 8, 12, 13 and interface cable port 14. When not in use, the openings are covered by flaps (not shown), with the flaps secured by velcro fasteners (not shown). The preferred material of protective cover 40 is nylon, which allows a user to easily slide portable device 9 underneath a patient as depicted in FIG. 9. In addition, nylon does not affect interfere with the X-ray entering the portable device. The material of protective device 40 is not limited to nylon, and any material that would allow practice of the present invention would be applicable.

Figure 12:
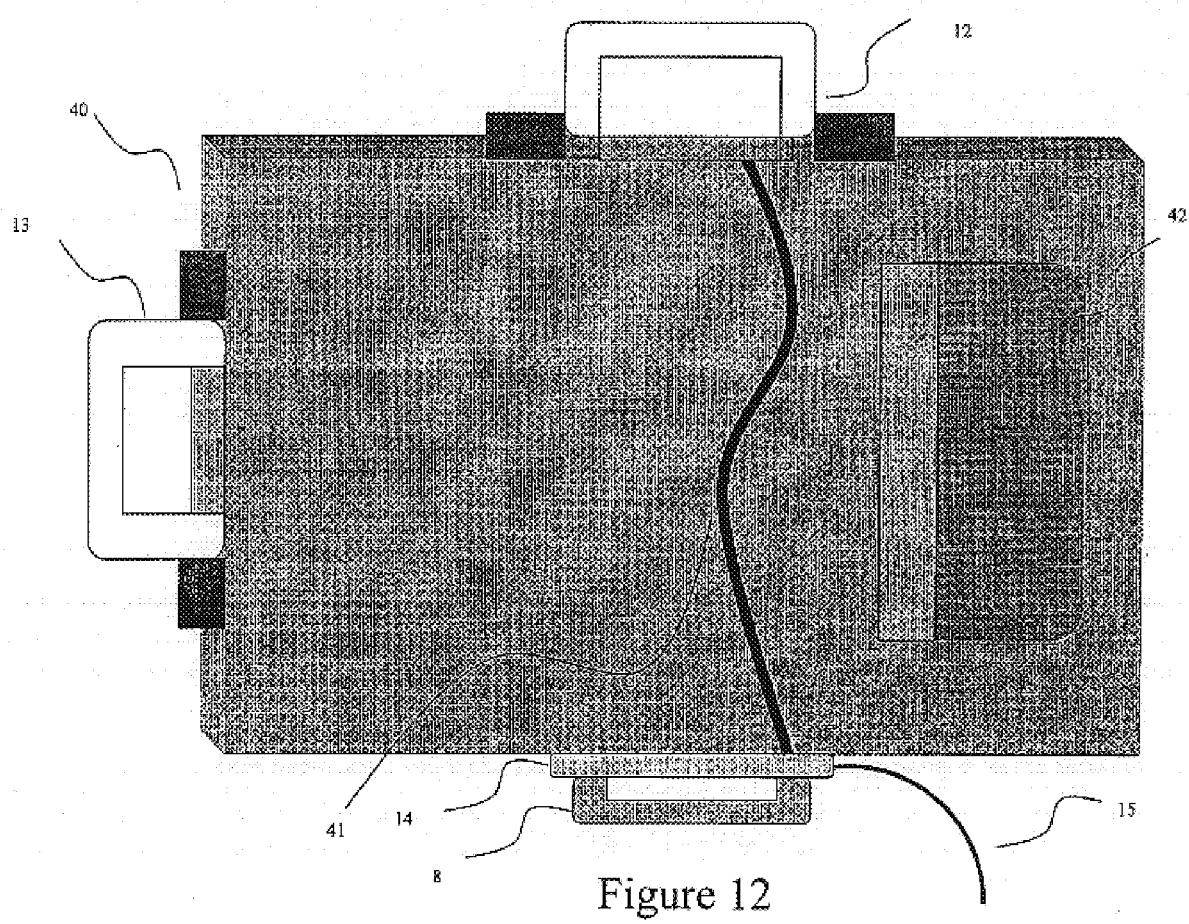
FIG. 12 depicts the back view of the first accessory to the portable device of the present invention in use with the portable device.

FIG. 12 depicts the back view of the protective cover 40. In more detail, FIG. 12 depicts carrying belt 41 and pocket 42. Carrying belt 41 and pocket 42 are used to carry portable device 9 from location to location. To carry portable device 9, a user would position an arm underneath carrying belt 41 and place a hand inside pocket 42. Pocket 42 provides a place for a user to hold portable device 9, while carrying belt 41 secures the user's arm to portable device 9. In addition, the combination of carrying belt 41 and pocket 42 can be used to help position portable device 9 in a situation where the use of handles 12, 13 may not be difficult.

Figure 13:
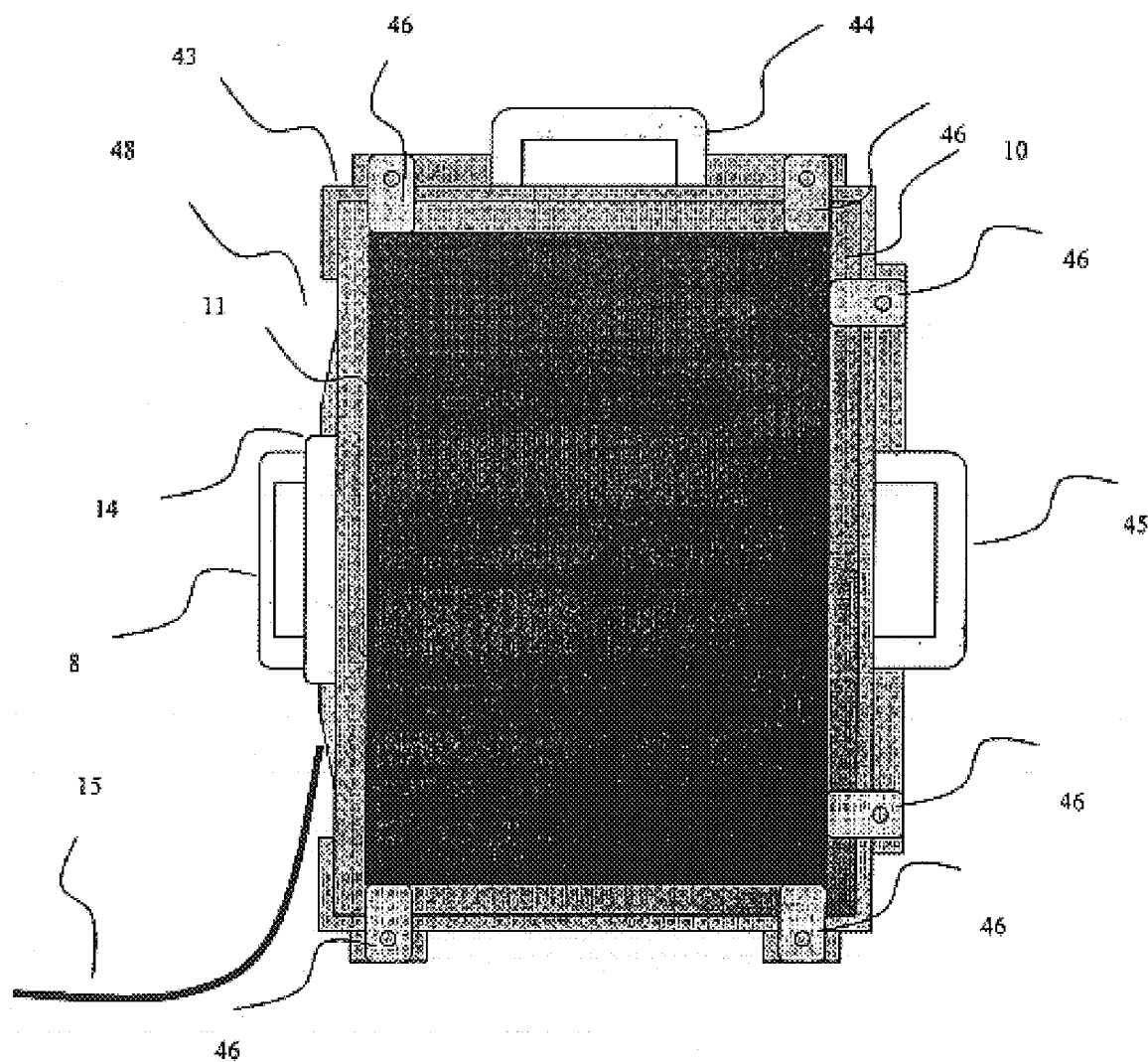
FIG. 13 is a top-down perspective of a second accessory to the portable device of the present invention in use with the portable device.

FIG. 13 is a top-down perspective of a second accessory to the portable device of the present invention in use with the portable device. More particularly, FIG. 13 depicts portable device 9 as described with respect to FIGS. 1 and 2. However, unlike portable device 9 depicted in FIGS. 1 and 2, portable device 48 of FIG. 13 does not include handles 12, 13. Rather, handles 44, 45 are secured to a separate frame 43 which can be secured to outer housing 10 of portable device 48. Frame 43 is secured to outer housing 10 via latching mechanism(s) 46. Handles 44, 45 are moveably connected to frame 43 in the same manner that handles 12, 13 are moveably connected to portable device 9. The preferred material of frame 43 handles 44, 45 and latching mechanism 45 is plastic, but is not limited to plastic and any material that would allow practice of the present invention would be applicable.

Figure 14:
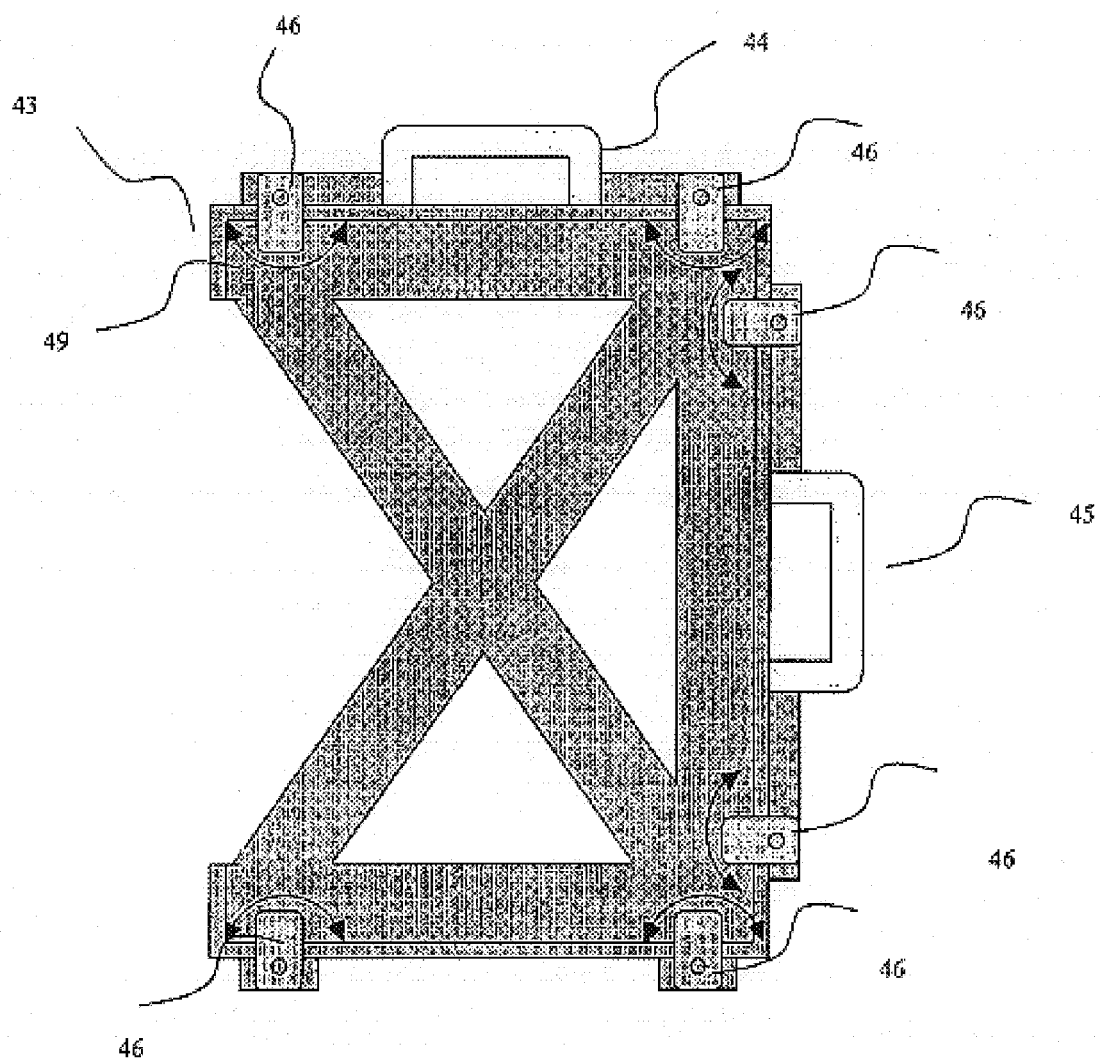
FIG. 14 is a stand-alone top-down perspective of the second accessory to the portable device of the present invention.

FIG. 14 is a stand-alone top-down perspective of frame 43 depicted in FIG. 13. Arrow 49 illustrates the motion of latching mechanism 46 used to secure frame 43 to outer housing 10 of portable device 9. A more detailed description of this motion is provided below with respect to FIG. 16.

Figure 15:
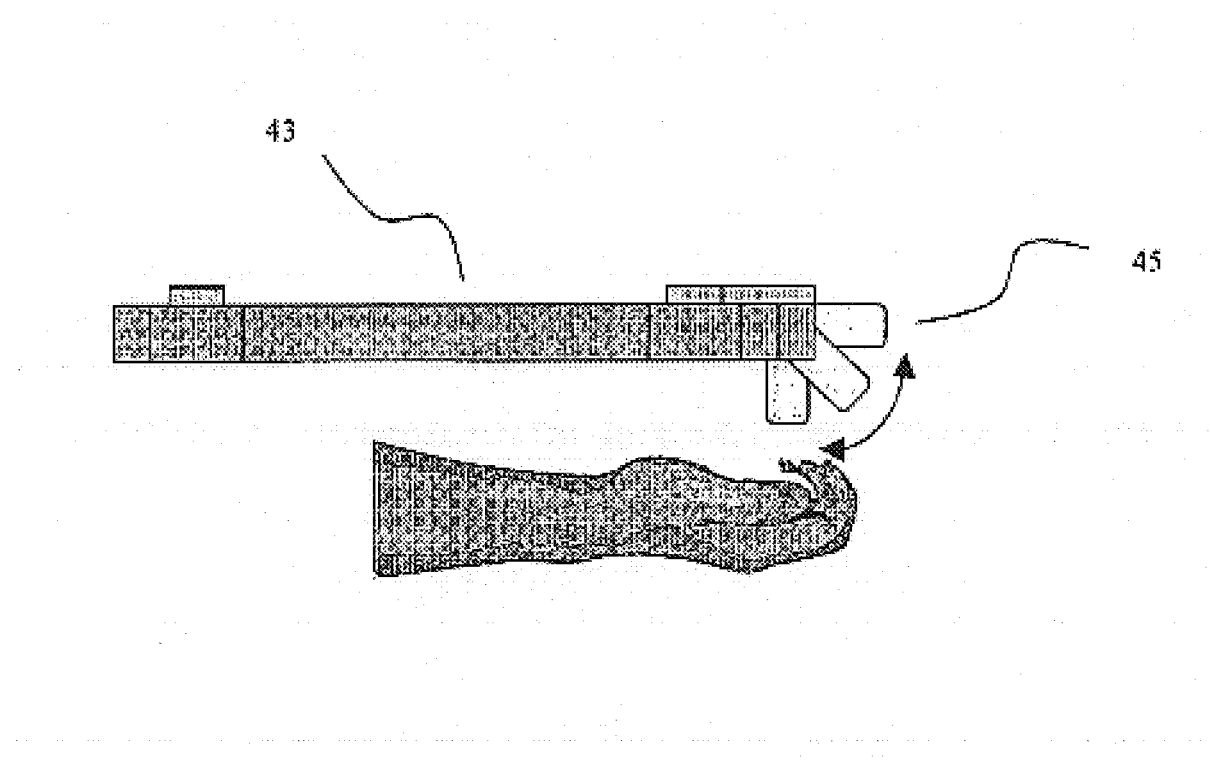
FIG. 15 is a side perspective of the second accessory to the portable device of the present invention.

FIG. 15 is a side perspective of frame 43. More specifically, FIG. 15 depicts movement of handle 45 with respect to frame 43. Movement of handle 45 with 5 respect to frame 43 is the same as the movement of handle 12 with respect to portable device 9 as described above.

Figures 16, 17:
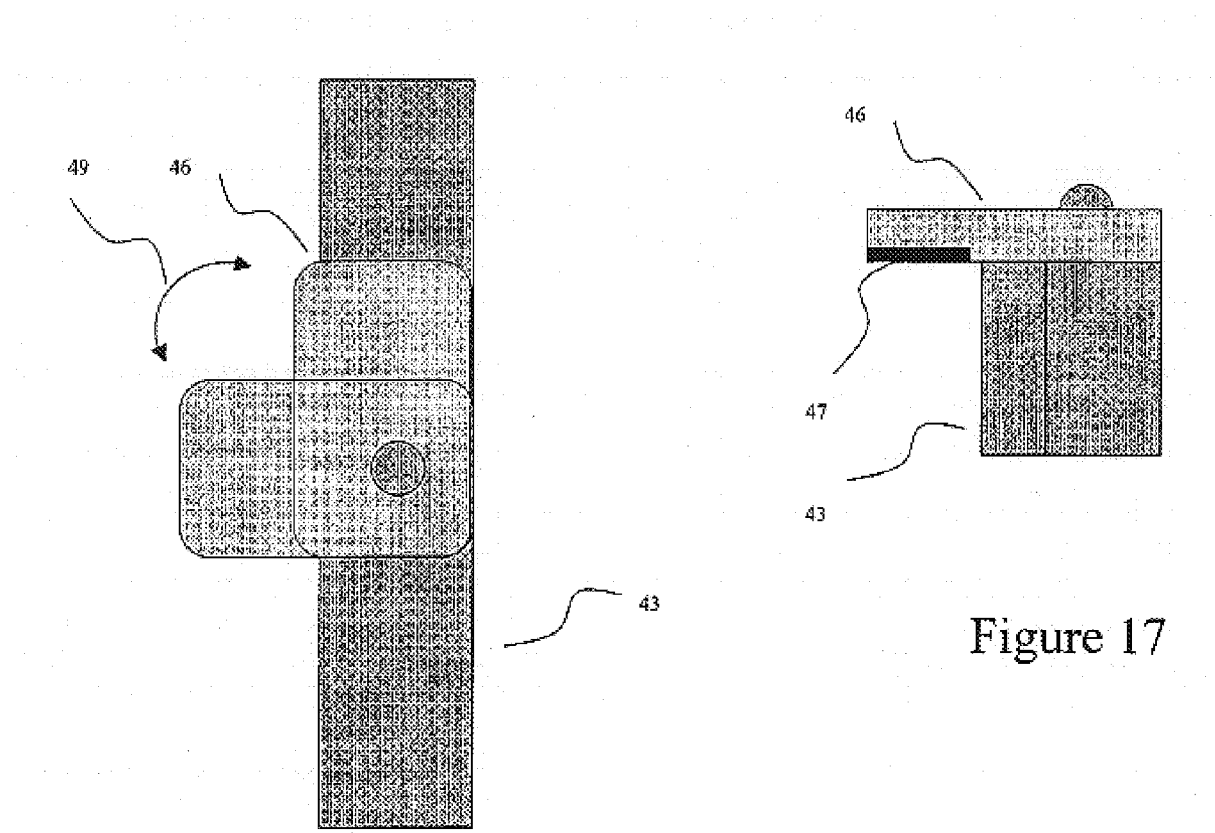
FIG. 16 is a top-down perspective depicting the movement of the latching mechanism of the second accessory to the portable device of the present invention.
FIG. 17 is side view of the latching mechanism of the present invention in the latched position.

FIG. 16 is a top-down perspective depicting movement of latching mechanism 46 with respect to frame 43. In more detail, when latching mechanism 46 is parallel to the plane of frame 43, frame 43 is not secured to outer housing 10 of portable 10 device 48. In order to secure or latch frame 43 to outer housing 10 of portable device 48, latching mechanism 46 is rotated to a position perpendicular to the plane of frame 43. To disengage or unlatch frame 43 from outer housing 10 of portable device 48, latching mechanism 46 is rotated back to a position parallel to the plane of frame 43.

FIG. 17 is side view of the latching mechanism of the present invention in the latched position. As shown in FIG. 17, the underside of latching mechanism 46 contains element 47. Element 47 is used to help maintain latching mechanism 46 in the secured or latched position. The preferred material of element 47 is rubber, as rubber will prevent damage to outer housing 10 of portable device 48 when latching mechanism is in the secured or latched position. However, any material which will maintain latching mechanism 46 in the secured or latched position and protect outer housing 10 of portable device 48 would be applicable.

The above embodiments describe the portable flat panel image detector of the present invention with respect to a digital radiography system. The application of the present invention is not limited to a digital radiography system and the invention may be used with other systems employing portable flat panel image detectors.

While the invention is described above with respect to what is currently its preferred embodiment, it is to be understood that the invention is not limited to that described above. To the contrary, the invention is intended to cover various modifications and equivalent arrangements within the spirit and scope of the appended claims.

What is claimed is:

1. A portable device for recording X-ray images, comprising:
    an X-ray image capture panel;
    a housing member connected to and surrounding the X-ray capture panel;
    at least a first handle secured to the housing member;
    means, movably connected to the at least first handle, for moving the handle from a position parallel to the plane of the device to a position perpendicular to the plane of the device and from a position perpendicular to the plane of the device to a position parallel to the plane of the device.

2. A portable device according to claim 1, wherein the at least first handle is secured to a horizontal side of the housing member.

3. A portable device according to claim 1, wherein the at least first handle is secured to a vertical side of the housing member.

4. A portable device according to claim 1, wherein the X-ray image capture panel is comprised of amorphous silicon and a thin film transistor array.

5. A portable device according to claim 1, wherein the housing member is comprised of plastic, aluminum, lead, and carbon.

6. A portable device according to claim 1, wherein the at least first handle is comprised of plastic.

7. A portable device according to claim 1, wherein at least a second handle is secured to the housing member.

8. A portable device according to claim 7, wherein the at least first handle is secured to a horizontal side of the housing member and the at least second handle is secured to a vertical side of the housing member.

9. A portable device for recording X-ray images, comprising:
    an X-ray image capture panel;
    a housing member connected to and surrounding the X-ray capture panel;
    at least a first handle secured to the housing member;
    means, movably connected to the at least first handle, for moving the handle from a position parallel to the plane of the portable device to a position perpendicular to the plane of the portable device and from a position perpendicular to the plane of the portable device to a position parallel to the plane of the portable device;
    retaining means for retaining the at least first handle in one of the parallel and perpendicular positions.

10. A portable device according to claim 9, wherein the at least first handle is secured to a horizontal side of the housing member.

11. A portable device according to claim 9, wherein the at least first handle is secured to a vertical side of the housing member.

12. A portable device according to claim 9, wherein the X-ray image capture panel is comprised of amorphous silicon and a thin film transistor array.

13. A portable device according to claim 9, wherein the housing member is comprised of plastic, aluminum, lead, and carbon.

14. A portable device according to claim 9, wherein the at least first handle is comprised of plastic.

15. A portable device according to claim 9, wherein at least a second handle is secured to the housing member.

16. A portable device according to claim 15, wherein the at least first handle is secured to a horizontal side of the housing member and the at least second handle is secured to a vertical side of the housing member.

17. A portable device according to claim 1, further including an accessory item in the form of a frame secured to the housing member.

18. An accessory item according to claim 17, wherein the frame is secured to a first side of the housing member.

19. An accessory item according to claim 17, wherein the frame is secured to a second side of the housing member.

20. An accessory item according to claim 17, wherein the frame is secured to a third side of the housing member.

21. An accessory item according to claim 17, wherein at least one handle is secured to the frame.

22. An accessory item according to claim 21, wherein the at least first handle is secured to a horizontal side of the frame.

23. An accessory item according to claim 21, wherein at least one handle is secured to a vertical side of the frame.

24. An accessory item according to claim 21, further comprising means moveably connected to the at least first handle for moving the handle from a position parallel to the portable device to a position perpendicular to the plane of the portable device and from a position perpendicular to the plane of the portable device to a position parallel to the plane of the portable device.

25. An accessory item according to claim 17, wherein the frame is comprised of plastic.

26. A portable device according to claim 1, further including an accessory item in the form of a cover.

27. A cover according to claim 26, wherein the cover comprises at least one opening on one side of the cover for placing the portable device inside the cover.

28. A cover according to claim 26, further comprising at least one flap extending from the cover for sealing the least one opening of the cover.

29. A cover according to claim 26, further comprising at least one opening on one side of the cover for the at least one handle.

30. A cover according to claim 26, further comprising at least one strap attached to the cover for carrying the cover.

31. A cover according to claim 26, further comprising at least one pocket on the exterior of the cover for carrying the cover.

32. A cover according to claim 26, wherein the interior and exterior fabric of the cover comprises nylon.

* * * * *